United States Patent [19]
Chang et al.

[11] 3,966,579

[45] June 29, 1976

[54] APPARATUS FOR MEASURING ALCOHOL CONCENTRATIONS

[76] Inventors: Kuo Wei Chang, 485 Massachusetts Ave., Lexington, Mass. 02173; Sol Aisenberg, 36 Bradford Road, Natick, Mass. 01760

[22] Filed: Mar. 20, 1974

[21] Appl. No.: 453,064

[52] U.S. Cl. .......................... 204/195 R; 136/86 R; 324/30 R
[51] Int. Cl.² ........................................ G01N 27/46
[58] Field of Search ............ 204/1 T, 195 R, 195 P, 204/1 K; 136/86 R, 86 D

[56] References Cited
UNITED STATES PATENTS

| | | |
|---|---|---|
| 3,149,921 | 9/1964 | Warner ............................ 204/1 T |
| 3,776,832 | 12/1973 | Oswin et al. .................... 204/195 R |
| 3,824,166 | 7/1974 | Deibert ........................... 204/195 R |
| 3,824,167 | 7/1974 | Oswin et al. .................... 204/195 R |

*Primary Examiner*—T. Tung
*Attorney, Agent, or Firm*—Nilsson, Robbins, Dalgarn & Berliner

[57] ABSTRACT

Alcohol concentrations present in a gaseous breath sample are monitored by measuring the magnitude of the short circuit current passing through the external circuit between the anode and cathode of a fuel cell. The anode and cathode are positioned on opposite sides of a cationic exchange membrane and an aqueous acid electrolyte between the cathode and membrane assists ion and electron transfer. Alcohol introduced at the anode is electrooxidized while oxygen supplied to the cathode is electroreduced.

11 Claims, 3 Drawing Figures

APPARATUS FOR MEASURING ALCOHOL CONCENTRATIONS

BACKGROUND OF THE INVENTION

This invention relates to analyzers, and specifically to an electrochemical fuel cell analyzer for measuring concentrations of alcohol in a breath sample.

The current emphasis for detection of blood-alcohol content is aimed at the drinking driver which, it is estimated, accounts for approximately 50 percent of all traffic fatalities occurring in the United States. However, current methods for measuring the alcohol concentrations in an individual's blood have proved to be either cumbersome or inaccurate. As a result, law enforcement agencies and others have sought a device capable of measuring an individual's blood-alcohol concentration by detecting alcohol concentrations in alveolar or deep lung air samples. The concentration of alcohol molecules in such breath samples has been found to be directly proportional to the concentration of alcohol in the individual's blood.

Currently available breath-alcohol instruments employ chemical reagents which interact with alcohol to determine the alcohol level by a colorimetric method. This type of analyzer, however, is relatively inaccurate, expensive and bulky as well as requiring an alternating current source and skilled personnel for its operation. Because of the lack of a portable quantitative instrument, the mobile law enforcement officer frequently does not make an arrest unless he first conducts a time consuming "field sobriety test" of coordination and reactions or the driver is unmistakably intoxicated. As a result, the majority of drivers whose motor functions may be severely impaired by alcohol are permitted to remain on the road at considerable risk to themselves and others.

Electrochemical detectors have been considered but to date investigation has been restricted to ordinary polarographic systems employing a cell with an anode, a counterelectrode and a reference electrode. The sensing anode in these systems is maintained at a predetermined voltage with respect to the reference electrode. An operational amplifier senses the potential difference between the reference and sensing electrodes to generate an error signal that determines the current flow between the counterelectrode and sensing electrode. This potential difference varies according to the rate of alcohol oxidation at the anode so that the current between electrodes changes in proportion to the alcohol concentration at the sensing electrode. However, a significant background current is always present in such systems, even in the absence of alcohol, frequently with magnitudes approaching the currents resulting from alcohol oxidation. Such background currents tend to be unstable due to changes in electrolyte concentration and electrode surface conditions, causing serious signal drift problems and other inaccuracies. In addition, the electrodes may become slowly deactivated by formation of oxides on their surfaces, and the reference electrode is subject to a continual degradation creating further long-term signal drift.

In contrast, the fuel cell breath-alcohol analyzer of this invention provides a compact, inexpensive and portable instrument that can be battery operated for field use. The cell itself operates without applying external electrical power because alcohol provides the fuel for generating the electrical signal current. Since no appreciable current flows through the cell in the absence of alcohol and no voltage difference need be maintained during cell operation, there is little, if any, background current, and the associated drift problems and other inaccuracies due to oxide formation and electrode degradation are virtually eliminated. Because the cell components are not consumed in the reaction, the cell has a practically unlimited life and is correspondingly simple and inexpensive to construct, operate and maintain. Furthermore, by operating in the alcohol diffusion limited mode, the short circuit current of the cell becomes linearly proportional to the alcohol concentration in an alveolar breath sample that corresponds directly with the individual's blood-alcohol concentration.

SUMMARY OF THE INVENTION

Alcohol molecules from a gaseous sample are electrooxidized at the active surface of a fuel cell anode while a cathode provides an active surface for electroreducing oxygen molecules. The anode and cathode are positioned on opposite sides of an ion exhange medium wherein an aqueous electrolyte provides a low impedance ion flow path. Alcohol molecules oxidized at the anode cause oxygen to be reduced at the cathode so that a short circuit current flows in the external circuit between the electrodes, which includes a low impedance current indicating means.

In the preferred embodiment of the invention, the anode consists of a material selected from the group consisting of platinum, nickel, palladium and tungsten carbide while the cathode consists of a material selected from the group consisting of platinum, palladium, silver and gold. A suitable permselective membrane allows oxygen to diffuse through to the cathode while excluding alcohol molecules that would react at the cathode. Another membrane limits the maximum diffusion rate of alcohol molecules reaching the anode so that all alcohol molecules contacting its active surface are readily electrooxidized. Thus, the short circuit current is linearly proportional to the concentration of alcohol in the breath sample under analysis.

DESCRIPTION OF THE INVENTION

While it is a primary object of this invention to measure the quantity of alcohol concentrations in alveolar breath samples, the exact quantity may be unimportant in other instances and breath concentrations of substances other than alcohol may be similarly detected, such as acetone in the breath of diabetics.

Specifically, the apparatus of this invention for quantitatively measuring concentrations of alcohol present in breath samples provides a low impedance ion exchange path between an anode and cathode which produces a short circuit current in an external circuit during the fuel cell reaction. The magnitude of the short circuit current is linearly proportional to the alcohol reaction rate at the anode. When the fuel cell is alcohol diffusion limited, the magnitude of the short circuit current is linearly proportional to the partial pressure of alcohol at the alcohol diffusion limiting membrane. An alcohol diffusion limited cell is obtained by separating the anode from the breath sample with a membrane which passes alcohol molecules to the anode at a maximum rate below the rate at which the anode begins to become unable to immediately oxidize all alcohol molecules reaching it.

Since the breath-alcohol concentration is at its maximum in alveolar breath, the magnitude of the short circuit current of such an alcohol diffusion limited cell will continue to increase until a maximum is reached when alveolar air enters the cell. This maximum short circuit current flow will be linearly proportional to the individual's blood-alcohol concentration.

Figure 1:
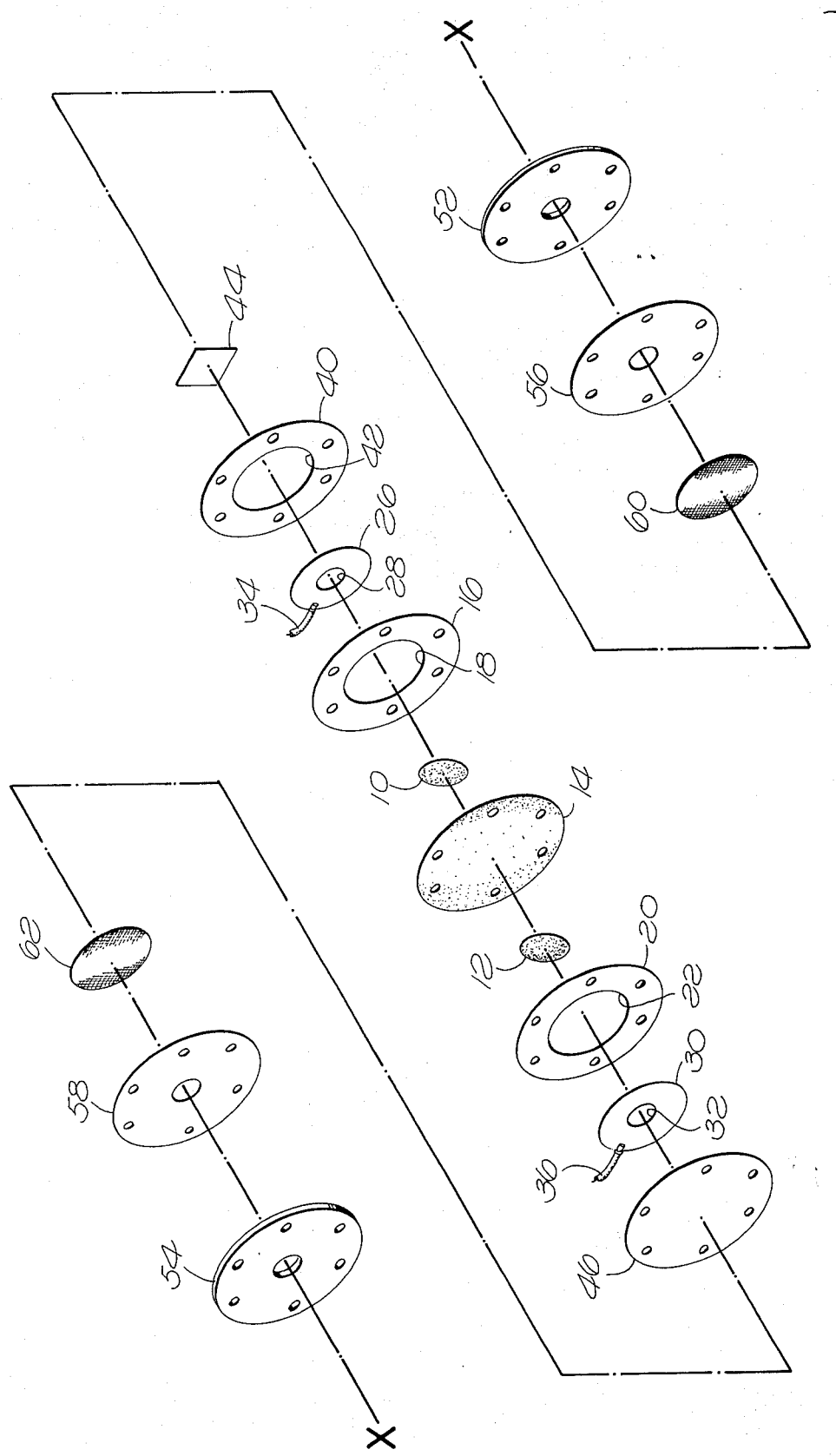
FIG. 1 is an exploded perspective view of the elements of the cell of one embodiment of the invention.
Figure 2:
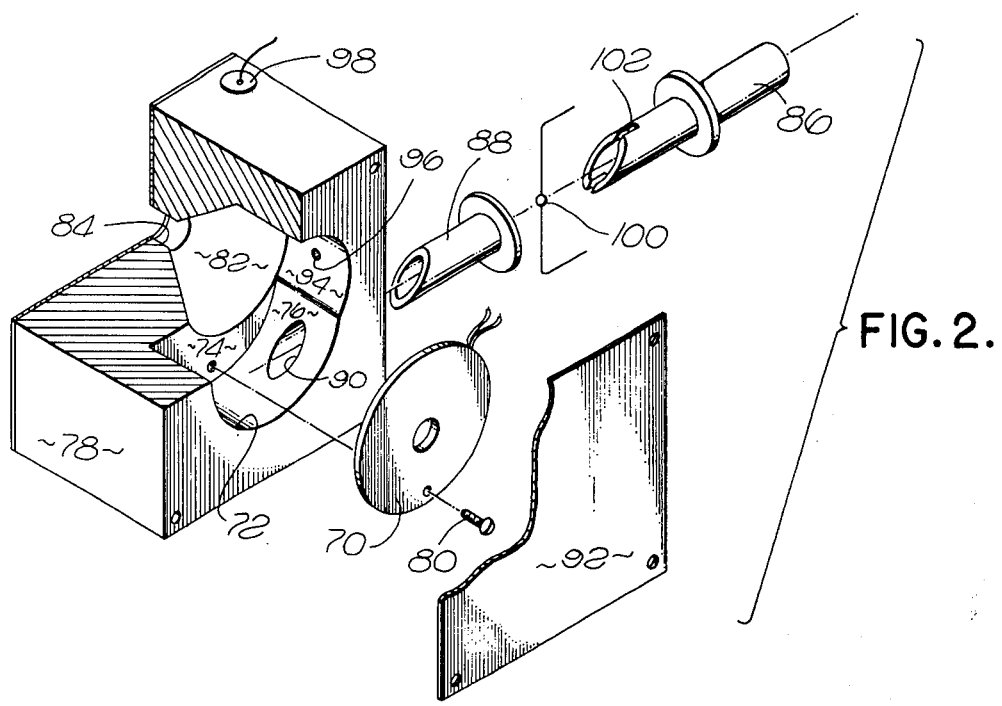
FIG. 2 is an exploded perspective view of the cell housing illustrating how the assembled cell of FIG. 1 and other components of one embodiment of this invention are assembled in the housing; and, FIG. 3 is a schematic block diagram showing the electrical system employed in one embodiment of this invention.

The operation of the analyzer of this invention will be more readily understood by reference to the accompanying drawing where FIG. 1 shows in detail the fuel cell sensing elements and adjacent components of one embodiment of this invention and FIG. 2 shows how these sensing elements, and various other mechanical commponents of the analyzer, are assembled to form a compact, portable alcohol breath analyzer. Each of these drawings may be referred to in the following description.

Although the electrodes may take many forms and shapes, in the preferred embodiment the anode 10 and cathode 12 are porous elliptical discs, each having a flat active surface pressed against opposite sides of cationic exhange membrane 14 compound of perfluorosulfonic acid Teflon or the like. The anode consists of a material, such as nickel, palladium or tungsten carbide, which will not deteriorate during fuel cell operation but which will oxidize alcohol in the presence of a compatible half-cell reaction at the cathode. Similarly, the cathode consists of a material, such as nickel, palladium, silver or gold, which will not deteriorate during fuel cell operation but which may reduce oxygen in the presence of the anode reaction. However, the material preferred for both electrodes is powdered platinum black mixed with a suitable binder, such as tetrafluoethylene (Teflon) powder, and a solvent in an aqueous dispersion. When this paste mixture is placed in a mold and heated to evaporate the solvent, the Teflon binds the platinum black powder together to form a porous sintered disc.

One side of cathode 12 is allowed to soak up quantity of an aqueous sulfuric acid solution so that when the electrodes 10 and 12 are pressed against opposite sides of the non-porous cationic membrane 14, the sulfuric acid electrolyte contacts and covers the adjacent area of the membrane and facilitates ion and electron transport between the two electrodes during fuel cell operation. The acid electrolyte is restricted to the cathode side of the membrane to avoid trapping alcohol molecules at the anode's active surface where they would affect the response time and accuracy of the cell.

In operation of the fuel cell sensing elements so far described, alcohol is oxidized upon contacting the platinum anode 10 to produce acetaldehyde, hydrogen ions, and free electrons while oxygen is electroreduced at the cathode in the presence of the hydrogen ions and free electrons to produce water. Since some of the water may permeate through the cationic membrane 14 to the anode and more moisture may be carried into the cell by the breath sample, the cell is maintained at a sufficiently high temperature to prevent condensation and to evaporate water, as will be explained hereinafter.

Two non-reactive discs 16 and 20, secured by adhesive or the like to the opposite sides of the cationic membrane 14, align the electrodes 10 and 12 positioned in the respective disc apertures 18 and 22 along a central cell axis X—X. The discs 16 and 20 are composed of an inert material, such as Teflon or the like. Ring shaped current collector plates 26 and 30 pressed into electrical contact with the peripheral surfaces of the anode and cathode respectively conduct the short circuit fuel cell current through wire leads 34 and 36 to the electrical system described hereinafter. The collector plate central apertures 28 and 32 have a circular diameter the same as the width of the elliptical electrodes 10 and 12 along their minor axes so that electrical contact is made at the inner edges of the collector plates while gases can pass through the apertures to the electrodes. Current collector plates 26 and 30 and the leads 34 and 36 are composed of a suitably inert electrically conductive material, such as platinum, gold, tantalum, or the like that does not react chemically with expected gases or the electrolyte.

Alcohol diffusion limiting membrane 44 is aligned within the central aperture 42 of spacer disc 40 to cover the current collector plate aperture 28 and limit the flow of alcohol reaching the anode. Spacer disc 40, composed of an inert material such as Mylar or the like, is adhesively bonded to the current collector plate 26 and disc 16 to maintain the apertures of the current collector plate and two discs in alignment along the X—X axis.

Membrane 44 may be porous or permselective depending upon the mode of operation. Suitable alcohol diffusion limiting permselective membranes amy consist of silicon rubber or dimethyl silicon rubber, and suitable porous membranes may consist of Teflon, polypropylene, cellulose acetate or the like. In a preferred embodiment of the invention, the permselective membrane is employed having a high diffusion rate for alcohol but a relatively low rate for interfering gases, and the cell is generally less sensitive to temperature changes than with porous membranes. In some cases, a plurality of membranes may be employed to obtain the required selectivity.

Such a cell may also be used to detect alcohol concentrations in mixtures other than breath samples. For example, blood specimens containing alcohol might be caused to flow over the membrane 44 in a suitably constructed cell so that the blood-alcohol concentration would be indicated directly.

If an alcohol diffusion limited cell is not required, such as where a signal need only indicate the presence or absence of alcohol, the membrane 44 may be removed since a measure of the quantity of alcohol in the gaseous sample is not important and the cell can thereby be made very sensitive to the presence of small quantities of alcohol.

Oxygen is supplied to the cathode 12 through membrane 46 which, in the preferred embodiment of the invention, is exposed both to the breath sample and to the atmosphere. As will become apparent hereafter, the breath sample supplants atmospheric oxygen at the membrane 46 during cell operation, thus providing an equivalent oxygen concentration at both the anode and cathode so that no signal is produced where there is an absence of alcohol in the breath sample. Oxygen could, however, be supplied from other sources, such as sealed tanks of oxygen gas.

In order to insure that alcohol molecules do not contact the cathode, membrane 46 is impermeable to alcohol but relatively permeable to the passage of oxygen. One such permselective membrane is composed of Teflon. If a pure oxygen source is employed, however, such as the tanks mentioned above, the membrane 46 is unnecessary.

The cell elements so far described are held together under compression between two rigid apertured end plates 52 and 54 which are composed of stainless steel or the like, apertured intermediate gaskets 56 and 58, and porous retaining screens 60 and 62. Retaining screen 60 fits snugly within spacer disc aperture 42 against membrane 44 and retaining screen 62 bears against the outer surface of oxygen permeable membrane 46 to compress the anode and cathode against opposite sides of cationic membrane 14. Gaskets 56 and 58 are composed of an inert, non-metallic material, such as polyethylene film, and the retaining screens 60 and 62 are preferably a metal mesh, such as a 50 line per inch tantalum screen or the like.

As is shown in FIG. 1, all of the elements so far described are aligned along a cell central axis X—X to allow passage of gases through the central apertures to the anode and cathode. These elements are retained together in alignment by screws of the like (FIG. 2) passing through peripherally spaced holes in various elements as shown in FIG. 1.

The assembled cell elements of FIG. 1, designated generally as 70 in FIG. 2, are secured against the crescent-shaped shoulder 74 of cell chamber 72 within aluminum mounting block 78 by screws 80 passing through the described peripheral screw holes in assembly 70. The peripheral edge of cell assembly 70 fits snugly against chamber wall 76 when in position except where notch 94 is formed, as will be described hereinafter. Cover plate 92 bolted to the mounting block seals the front of chamber 72.

A conical oxygen chamber 82 eccentrically formed in the mounting block's rear wall provides access for supplying oxygen and for exhausting breath samples through vent 84. An alcohol bearing breath sample is conducted through mouthpiece 86 and insert 88, composed of Teflon or the like and secured in inlet port 90, into the cell chamber 72 where alcohol molecules pass across the face of the cell, some permeating through membrane 44 to contact anode 10 in proportion to the partial pressure of alcohol in the sample. Outlet port 94, cut in chamber wall 76, conducts the gas sample out of the cell chamber through conical chamber 82 and vent 84. At the same time, the oxygen bearing breath sample in chamber 82 contacts membrane 46 as has been previously described. The inlet and outlet ports are positioned so that the breath sample enters the cell chamber tangentially creating a whirlpool flow action across the cell face to minimize dilution of the entering breath sample by gas already in the chamber.

The alcohol molecules exiting through conical chamber 82 are prevented from entering the oxygen side of the cell by the previously described permselective membrane 46 that is selectively impermeable to the passage of alcohol. The current collector plate leads 34 and 36 are conducted outside of mounting block 78 through a hole 96 drilled through block 78 into notch 94.

Where a volumetric measurement is required in conjunction with the detection of breath-alcohol concentrations, a device such as a rubber balloon may be filled with the breath sample and then attached to the mouthpiece 86. If a continuous measurement is desired, an individual may blow into a disposable rubber tube (not shown) connected to mouthpiece 86. In either case, a saliva trap should be employed to remove moisture contained in the breath sample which might reach the anode and produce inaccurate readings by trapping alcohol molecules. In addition, since the sensor is dependent upon the partial pressure of alcohol, a restriction (not shown) is employed before the breath sample enters chamber 72 and the outlet notch 94 and vent 84 are made large enough to insure that breath samples can pass from the cell chamber at least as rapidly as the sample enters the chamber in order to avoid pressure build-up in the cell chamber which might distort the alcohol concentration measurements. The membrane 44 may also be thick enough to slow down the passage of alcohol molecules in order to reduce erroneous readings resulting from high pressures at the beginning of an individual's exhale cycle into the sample chamber.

Heating element 98, consisting of a stainless steel sleeve surrounding a chromium wire or the like, is inserted into mounting block 78 to maintain the cell at the desired temperature. This temperature is detected by thermistor 100 held in position at the breath outlet end of mouthpiece 86 by wire leads threaded through slots 102 in the mouthpiece. In the preferred embodiment of the invention, the cell is maintained at 34°C or above when not in use in order to prevent moisture condensation and to evaporate water that might form at the anode. In addition, the cell chamber temperature is normally maintained at about 50°C so that a breath sample passing across thermistor 100 causes its temperature to decrease at a rate proportional to the velocity of the breath flow. The resulting change in the thermistor resistance connected in a bridge circuit varies the voltage applied to a volumetric flow detector circuit, described hereinafter, to indicate when sufficient quantities of air have been expelled from the lungs to insure that alveolar air is entering the cell chamber.

In order to clear the cell chamber 72 of alcohol after each use, a jet of ambient air is blown through the mouthpiece 86 with a rubber bulb or the like attached to the mouthpiece 86 after each test.

As has been previously mentioned, the sensor of this invention can be made sensitive to other gases, such as acetone carried in the breath of diabetic patients. However, the signal produced by oxidizing acetone with the described sensor is relatively insignificant when compared with the signal produced by alcohol so that alcohol should be removed from acetone breath sample before any acetone measurements are made.

While inert materials other than those mentioned for use as anode 10 might be employed, platinum has been found to produce maximum signal current due to its catalytic activity with alcohol. Gases other than oxygen may be reduced at the cathode as long as the selected material is capable of reduction to give up negative free energy. In this connection, the cathode material used must of course be able to reduce the gaseous substance supplied and be otherwise compatible in the overall system. The platinum-oxygen half-cell has been found to be most satisfactory and compatible with the platinum-alcohol half-cell. Furthermore, basic or neutral electrolytes may replace the sulfuric acid electrolyte and the electrolyte may be present in the anode. As an example, with platinum as the anode, gold may be employed as the cathode and a basic solution of potassium hydroxide may replace the sulfuric acid electrolyte. However, sulfuric acid is the preferred electrolyte since, among other things, it does not evaporate at the temperatures where water may be driven off.

Figure 3:
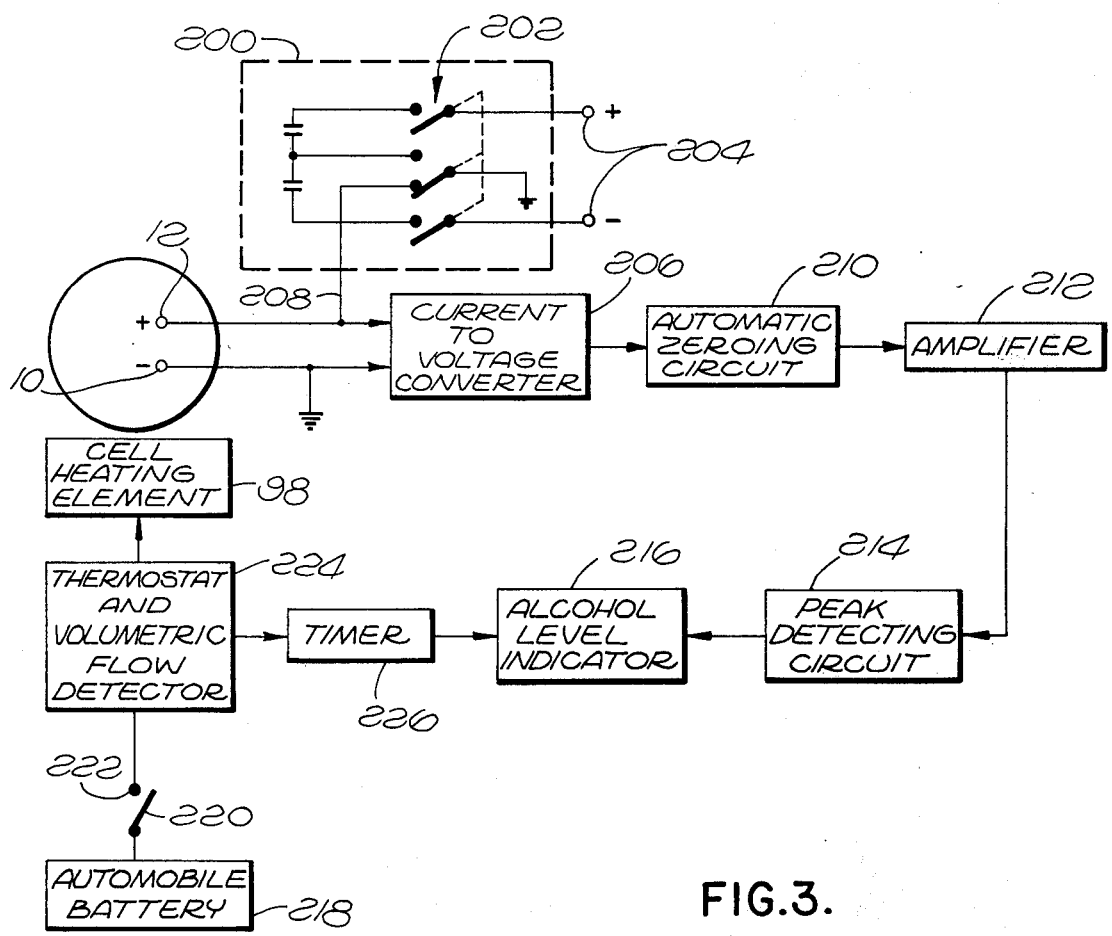

FIG. 3 shows the electrical system employed in a preferred embodiment of this breath-alcohol analyzer to convert the cell short circuit current to a voltage output and hold the highest voltage level attained, since it is that voltage level which is proportional to the individual's blood-alcohol concentration.

Regulated power supply 200 delivers a constant voltage to the circuit when switch 202 is moved to its "on" position to connect the terminals 204 to the power supply. The regulated power supply may be, for example, rechargeable batteries providing a constant 5 volts across the circuit terminals 204.

The short circuit current output of the cell is typically in the microampere range so that a low input impedance operational amplifier is employed as a current-to-voltage converter 206. In such a configuration, it has been found that a small background voltage exists across the operational amplifier input. In this condition, connecting the power supply 200 into the circuit generates an amplified current pulse output that is fed back to the cell which then acts as a capacitor in storing a charge that may place a substantial voltage across the cell adversely affecting future cell accuracy. Thus, when the analyzer is not in use, the positive cathode and negative anode are always shorted together to ground through line 208 to equalize the electrode voltages. Also, an adjustable trimmer, such as a potentiometer, is connected in the current-to-voltage converter circuit to keep the cell voltage at a low level, such as between 0–50 microvolts, to prevent distortion of the cell response.

An automatic zeroing circuit 210 may be used to eliminate the effects of any background current from the output signal of current-to-voltage converter 206. This is accomplished, for example, by supplying a negative feedback signal that cancels the input to an operational amplifier to maintain a zero output until the breath sample is present. The feedback path is then disconnected before the breath sample is received while holding the feedback signal voltage across a capacitor at the input of the operational amplifier.

The gain of a second stage signal amplifier 212 may be adjusted to produce an output signal of a desired amplitude to drive a selected indicator 216. The output of amplifier 212 is provided to peak detecting circuit 214 which may consist of a diode and a buffer operational amplifier in series with the alcohol level indicator 216 and a holding capacitor connected between them to ground. Peak detecting circuit 214 maintains a constant amplitude output proportional to the maximum output signal level from amplifier 212 and holds this output level as the cell short circuit current decreases with lower alcohol concentrations in the cell chamber 72. Thus, the peak detecting circuit 214 maintains the signal to the alcohol level indicator 216 at a magnitude indicative of the highest breath-alcohol concentration encountered during each test. Alcohol level indicator 216 may be a voltmeter, multicolored lights, or the like with a graduated scale indicating various alcohol concentration levels.

When the analyzer is not in use, it is placed in a cradle having a separate power supply to maintain the desired cell temperature level previously described. Where the analyzer is used by law enforcement agencies, for example, the cradle may be located in a patrol vehicle. In such an arrangement, a contact switch 220 in the cradle is connected to the automobile battery 218 so that when the analyzer is placed in the cradle, the automobile battery will be automatically connected to the cell heating element 98 through analyzer contact 222 and the thermostat and volumetric flow detector 224.

As has been previously described, thermistor 100 detects both the temperature within the cell chamber 72 and any drop in temperature caused by a breath sample entering the cell chamber. The thermistor triggers the thermostat circuit to connect the automobile battery 218 with the heating element 98 whenever the cell chamber temperature drops below the desired level. In addition, when a breath sample passes through the mouthpiece into the cell chamber, the thermistor is temporarily cooled causing a voltage change in the volumetric flow detector circuit that initiates operation of a timer 226. The timer delays activation of alcohol level indicator 216 to insure that the indicator, when activated, will present an indication of the highest cell output that will be obtained during that test. For example, if the cell output typically does not reach its peak value for about thirty seconds after the breath sample is introduced, the timer might be set to delay the indicator for about 45 seconds so that the person reading the indicator is sure that the alcohol level displayed is at its highest level expected.

In addition, the volumetric flow detector may be constructed to require minimum volume of breath to pass through the mouthpiece before the timer is initiated, thereby insuring that alveolar air is introduced into the sensor.

In operation, the current-to-voltage converter is initially adjusted so that the offset voltage is maintained between 0–50 microvolts. Upon removal from the cradle, the analyzer has an internal temperature of about 50°C. When power switch 202 is closed to connect regulated power supply 200 to the circuit through terminals 204, automatic zeroing circuit 210 corrects for any background current by zeroing the signal to amplifier 212. A breath sample is introduced into the cell through mouthpiece 86 after passing through a disposable tube that restricts breath inflow below the cell chamber outlet capacity and traps any saliva. When enough of the breath sample has passed across thermistor 100, timer 226 is started and upon completion of the timing cycle, activates alcohol level indicator 216 as the cell output approaches its peak level.

The cell output is converted to a voltage signal and passed through automatic zeroing circuit 210 where the existing background signal is cancelled. After amplification, peak detecting circuit 214 holds the output signal at its maximum level to provide continuous peak signal input to the alcohol level indicator where the alcohol level concentration in the breath sample is displayed when actuated by timer 226.

After use, the cell is cleared of alcohol by passing fresh air through the cell chamber 72 and the circuit components are reset by moving switch 202 to its off position. The analyzer is returned to its cradle where battery 218 powers the heating element to maintain the desired cell chamber temperature, as detected by thermistor 100, to evaporate liquids which might have formed in the chamber.

It will be apparent from the foregoing that various modifications may be made without departing from the scope of the invention. For example, various changes could be made in the shapes and sizes of the cell elements and different electrical systems may be employed, so that the invention is not limited to the specific embodiments employed herein to describe the invention.

What is claimed is:

1. An electrochemical fuel cell analyzer for detecting the presence of alcohol, comprising:
   an anode having an active catalytic surface for electrooxidizing impinging alcohol molecules;
   a cathode having an active catalytic surface for electroreducing oxygen molecules;
   ion exchange means impermeable to electrolyte separating said anode and cathode positioned on opposite sides thereof;
   an aqueous electrolyte maintained between said anode and cathode active surfaces; and,
   low impedance circuit means connected between said anode and cathode substantially eliminating voltage differences across said cell to provide a short circuit current output and includes means for measuring the flow of said short circuit current
   whereby a low impedance ion exchange path is formed in said cell between said anode and cathode upon oxidation of alcohol at said anode and reduction of oxygen at said cathode.

2. An electrochemical fuel cell analyzer for detecting the presence of alcohol in a breath sample, comprising:
   an anode having an active surface consisting of a material selected from the group consisting of platinum, nickel, palladium, and tungsten carbide for electrooxidizing impinging alcohol molecules;
   a cathode having an active surface consisting of a material selected from the group consisting of platinum, nickel, palladium, silver and gold for electroreducing oxygen molecules;
   an ion exchange barrier impermeable to electrolyte and separating the anode and cathode positioned on opposite surfaces thereof;
   an aqueous acid electrolyte contained between said cathode and ion exchange barrier and wetting said active cathode surface and contacting the adjacent surface of said ion exchange barrier to facilitate ion and electron transfer between said anode and cathode; and,
   low impedance circuit means connecting said anode and cathode substantially eliminating voltage differences across said cell to provide a short circuit current output and including means for measuring the flow of said short circuit current,
   whereby a low impedance ionic current path is formed in said cell between said anode and cathode upon oxidation of alcohol at said anode and reduction of oxygen at said cathode.

3. A fuel cell analyzer as defined in claim 2 wherein said electrolyte comprises sulfuric acid, and further comprising:
   a cell structure for conveying alcohol molecules in a breath sample to said anode and providing oxygen molecules without alcohol to said cathode.

4. A fuel cell analyzer as defined in claim 3 wherein: said anode and cathode both comprise porous platinum discs.

5. A fuel cell analyzer as defined in claim 4 wherein: said ion exchange barrier comprises a cationic exchange membrane and said aqueous acid electrolyte wets both the active surface of the cathode and the adjacent surface of said cationic exchange membrane against which said cathode is pressed.

6. A fuel cell analyzer as defined in claim 5 further comprising:
   membrane means adapted to limit the maximum rate of alcohol molecules reaching the anode to a level below the maximum oxidation reaction capacity of said anode so that said short circuit current is diffusion limited to be linearly proportional to the concentration of alcohol in said sample; and wherein,
   said low impedance circuit means includes negative feedback means for cancelling background current signals generated by the cell.

7. A fuel cell analyzer as defined in claim 6, wherein: said low impedance circuit means comprises a low input impedance current amplifier with a gain greater than zero and having a trimmer circuit for substantially eliminating voltage differences across the cell.

8. A fuel cell analyzer as defined in claim 7, further comprising:
   means for heating said cell to a temperature of at least about 34° centigrade prior to sensing alcohol to prevent condensation and to evaporate alcohol retaining liquids.

9. A fuel cell analyzer as defined in claim 7, wherein: said amplifier operated as a current-to-voltage converter.

10. A fuel cell analyzer as defined in claim 7 wherein said low impedance circuit means further comprises:
    means for indicating the measured short circuit current; and,
    timer means for detecting the conveyance of a breath sample to said fuel cell and delaying operation of said indicating means sufficiently to insure that alveolar air has been conveyed to the fuel cell.

11. An electrochemical fuel cell analyzer for detecting the presence of alcohol, comprising:
    an anode having an active surface consisting of a material selected from the group consisting of platinum, nickel, palladium, and tungsten carbide for electrooxidizing impinging alcohol molecules;
    a cathode having an active surface consisting of a material selected from the group consisting of platinum, nickel, palladium, silver and gold for electroreducing oxygen molecules;
    an ion exchange barrier impermeable to electrolyte and separating the anode and cathode positioned on opposite surfaces thereof;
    an aqueous acid electrolyte contained between said cathode and ion exchange barrier and wetting said active cathode surface and contacting the adjacent surface of said ion exchange barrier to facilitate ion and electron transfer between said anode and cathode;
    low impedance circuit means connecting said anode and cathode substantially eliminating voltage differences across said cell to provide a short circuit current output and including means for measuring the flow of said short circuit current,
    whereby low impedance ionic current path is formed in said cell between said anode and cathode upon oxidation of alcohol at said anode and reduction of oxygen at said cathode;

first membrane means adapted to limit the maximum rate of alcohol molecules reaching the anode to a level below the maximum oxidation reaction capacity of said anode so that said short circuit current is diffusion limited and linearly proportional to the concentration of alcohol in said sample;

second membrane means adapted to exclude alcohol molecules from reaching the cathode; and, means for heating said cell to a temperature of at least about 34° centigrade prior to sensing alcohol to prevent condensation and to evaporate alcohol retaining liquids.

* * * * *

UNITED STATES PATENT AND TRADEMARK OFFICE
CERTIFICATE OF CORRECTION

PATENT NO. : 3,966,579
DATED : June 29, 1976
INVENTOR(S) : Kuo Wei Chang and Sol Aisenberg It is certified that error appears in the above-identified patent and that said Letters Patent are hereby corrected as shown below:

Col. 2, line 33, after "platinum," add --nickel,--.

Col. 3, line 33, change "compound" to --composed--.

Col. 3, line 40, change "may" to --will--.

Col. 4, line 36, change "amy" to --may--.

Col. 5, line 28, change "of" to --or--.

Col. 6, line 55, after "from" add --any--.

Col. 7, line 52, change "ouput" to --output--.

Signed and Sealed this

Twelfth Day of October 1976

[SEAL]

Attest:

RUTH C. MASON
*Attesting Officer*

C. MARSHALL DANN
*Commissioner of Patents and Trademarks*